United States Patent
Madhukar Kodgule et al.

(10) Patent No.: US 9,446,032 B2
(45) Date of Patent: Sep. 20, 2016

(54) METHODS FOR TREATING CARDIOVASCULAR DISORDERS

(75) Inventors: Mandar Madhukar Kodgule, Aurangabad (IN); Premchand Dalichandji Nakhat, Noida (IN); Amit Gupta, Ahmedabad (IN); Girish Kumar Jain, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 94 days.

(21) Appl. No.: 14/240,380

(22) PCT Filed: Aug. 23, 2012

(86) PCT No.: PCT/IB2012/054257
§ 371 (c)(1),
(2), (4) Date: May 15, 2014

(87) PCT Pub. No.: WO2013/030725
PCT Pub. Date: Mar. 7, 2013

(65) Prior Publication Data
US 2014/0302125 A1    Oct. 9, 2014

(30) Foreign Application Priority Data

Aug. 26, 2011 (IN) .................. IN2011MU2395A
Aug. 26, 2011 (IN) .................. IN2011MU2399A
Aug. 27, 2011 (IN) .................. IN2011MU2411A

(51) Int. Cl.
| A61K 9/22 | (2006.01) |
| A61K 31/4418 | (2006.01) |
| A61K 31/138 | (2006.01) |
| A61K 31/40 | (2006.01) |
| A61K 31/41 | (2006.01) |
| A61K 45/06 | (2006.01) |

(52) U.S. Cl.
CPC .......... *A61K 31/4418* (2013.01); *A61K 31/138* (2013.01); *A61K 31/40* (2013.01); *A61K 31/41* (2013.01); *A61K 45/06* (2013.01)

(58) Field of Classification Search
CPC .......... A61K 9/14; A61K 9/141; A61K 9/16; A61K 9/1605; A61K 9/2072; A61K 9/2086; A61K 9/1652; A61K 9/167; A61K 9/20; A61K 9/2004; A61K 9/2054; A61K 9/48
USPC ................................... 424/465–489
See application file for complete search history.

(56) References Cited

U.S. PATENT DOCUMENTS

| 4,942,040 | A | * | 7/1990 | Ragnarsson | ......... | A61K 9/2081 |
| | | | | | | 424/459 |
| 2005/0032879 | A1 | | 2/2005 | Okarter et al. | | |
| 2008/0233190 | A1 | * | 9/2008 | Solomon | ............. | A61K 9/2072 |
| | | | | | | 424/467 |

FOREIGN PATENT DOCUMENTS

| CN | 101249083 A | 8/2008 | | |
| WO | WO2007/010501 A2 | 1/2007 | | |
| WO | WO 2007010501 A2 * | 1/2007 | .......... | A61K 9/2081 |
| WO | WO2007/110753 A2 | 9/2007 | | |

OTHER PUBLICATIONS

Efficacy and tolerability of a fixed-dose combination of metoprolol extended release/amlodipine in patients with mild-to-moderate hypertension: a randomized, parallel-group, multicentre comparison with losartan plus amlodipine. Pareek et al., Clin Drug Investig. 2010;30(2):123-131.

A clinical trial to study the effects of two drugs Olmesartan and metoprolol in patients with high blood pressure and heart disease. Mohan. Clinical Trials Registry—India, Aug. 8, 2011. [retrieved on Nov. 23, 2012]. cited in the application and in the International Search Report.

* cited by examiner

*Primary Examiner* — Micah-Paul Young
(74) *Attorney, Agent, or Firm* — Bio Intellectual Property Services LLC (Bio IPS); O. (Sam) Zaghmout

(57) ABSTRACT

There is provided a once-a-day therapeutically synergistic pharmaceutical dosage form for treatment of cardiovascular disorders, wherein the dosage form comprises a fixed dose combination of metoprolol in extended release form and one or more calcium channel blocker, angiotensin II receptor blocker or angiotensin converting enzyme inhibitor along with one or more rate controlling excipient.

7 Claims, No Drawings

METHODS FOR TREATING CARDIOVASCULAR DISORDERS

FIELD OF THE INVENTION

The present invention relates to a once-a-day therapeutically synergistic pharmaceutical dosage form for treatment of cardiovascular disorders, wherein the dosage form comprises a fixed dose combination of metoprolol in extended release form and one or more calcium channel blocker, angiotensin II receptor blocker or angiotensin converting enzyme (ACE) inhibitor along with one or more rate controlling excipient.

BACKGROUND OF THE INVENTION

"Cardiovascular disease or disorder" is intended to mean any cardiovascular disease or disorder known in the art, including congestive heart failure, complications associated with diabetes mellitus, hyperhomocysteinemia, hypercholesterolemia, atherosclerosis, inflammatory heart disease, valvular heart disease, restenosis, hypertension (e.g. pulmonary hypertension, labile hypertension, idiopathic hypertension, low-renin hypertension, salt-sensitive hypertension, low-renin, salt-sensitive hypertension, thromboembolic pulmonary hypertension; pregnancy-induced hypertension; renovascular hypertension; hypertension-dependent end-stage renal disease, hypertension associated with cardiovascular surgical procedures, hypertension with left ventricular hypertrophy, and the like), diastolic dysfunction, coronary artery disease, myocardial infarctions, cerebral infarctions, arteriosclerosis, atherogenesis, cerebrovascular disease, angina (including chronic, stable, unstable and variant (Prinzmetal) angina pectoris), aneurysm, ischemic heart disease, cerebral ischemia, myocardial ischemia, thrombosis, platelet aggregation, platelet adhesion, smooth muscle cell proliferation, vascular or non-vascular complications associated with the use of medical devices, vascular or non-vascular wall damage, peripheral vascular disease, neointimal hyperplasia following percutaneous transluminal coronary angiograph, vascular grafting, coronary artery bypass surgery, thromboembolic events, post-angioplasty restenosis, coronary plaque inflammation, embolism, stroke, shock, arrhythmia, atrial fibrillation or atrial flutter, thrombotic occlusion and reclusion cerebrovascular incidents, and the like.

Many individuals are at an elevated risk of suffering serious to life-threatening cardiovascular events, including infarction (heart attack), cardiac arrest, congestive heart failure, stroke, peripheral vascular disease and/or claudication. The risk factors are numerous and widespread throughout the world population. They include cigarette smoking, diabetes, hypercholesterolemia (high serum cholesterol), hypertension, angina, systemic lupus erythematosus, prior heart attacks or strokes, hemodialysis, hyperhomocysteine levels, obesity, sedentary lifestyle, receiving an organ transplant, atherosclerosis, and others. There is a need for a safe and convenient pharmaceutical formulation that would effectively reduce the risk of incurring a cardiovascular event in individuals who have these risk factors.

The treatments and drugs discovered or known in the art for cardiovascular disease includes but are not limited to beta-blockers, for example, atenolol, metoprolol, nadolol, oxprenolol, pindolol, propranolol, timolol; Alpha blockers, for example, doxazosin, phentolamine, indoramin, phenoxybenzamine, prazosin, terazosin, tolazoline; mixed alpha and beta blockers, for example, bucindolol, carvedilol and labetalol.

Beta-blocker, for example, metoprolol acts by blocking the adrenergic stimulation of the heart and thus reduces the oxygen demand of the cardiac tissue. Apparently, this explains their beneficial effects in angina pectoris and cardioprotective action in myocardial infarction. In addition, beta-blockers normalize blood pressure in a large proportion of patients with arterial hypertension, which probably is due to an additional action on the control of peripheral resistance to blood-flow.

Metoprolol (Formula I) is a beta1-selective (cardioselective) adrenoreceptor-blocking agent. It is commercially available in two salt forms; one of them is tartrate salt available as Lopressor® tablets and the other is succinate salt available as Toprol®-XL tablets. The Toprol®-XL tablets contain 23.75 mg, 47.5 mg, 95 mg and 190 mg of metoprolol succinate equivalent to 25 mg, 50 mg, 100 mg and 200 mg of metoprolol tartrate, USP, respectively. Metoprolol is indicated in the treatment of hypertension, heart failure and angina pectoris.

Initial therapy with a diuretic or beta-blocker has been the usual first approach for treating cardiovascular disorders. ACE inhibitors, calcium channel blockers and angiotensin receptors blockers are also effective as first-line therapy. The physician is therefore required to choose from above classes of agents for initial therapy.

Calcium channel blockers play important role in contractile processes of cardiac muscle and vascular smooth muscle by regulating the movement of extracellular calcium ions into these cells through specific ion channels. Calcium channel blockers work by blocking voltage-gated calcium channels (VGCCs) in cardiac muscle and blood vessels. This decreases intracellular calcium leading to a reduction in muscle contraction. In the heart, a decrease in calcium available for each beat results in a decrease in cardiac contractility. In blood vessels, a decrease in calcium results in less contraction of the vascular smooth muscle and therefore an increase in arterial diameter (CCBs do not work on venous smooth muscle) a phenomenon called vasodilation.

Angiotensin II receptor blockers (ARBs), also known as angiotensin II receptor antagonists, AT1-receptor antagonists or "sartans", are a group of drugs which modulate the renin-angiotensin-aldosterone system. Their main uses are in the treatment of hypertension (high blood pressure), diabetic nephropathy (kidney damage due to diabetes) and congestive heart failure. Angiotensin II receptor blockers, block the activation of angiotensin II AT1 receptors. Blockade of AT1 receptors directly causes vasodilation, reduces secretion of vasopressin, and reduces production and secretion of aldosterone, amongst other actions. The combined effect reduces blood pressure.

ACE inhibitors or angiotensin-converting enzyme inhibitors are a group of drugs used primarily for the treatment of hypertension (high blood pressure) and congestive heart failure, although they may also be prescribed for cardiac failure, diabetic nephropathy, renal disease, systemic sclerosis, left ventricular hypertrophy and other disorders. Originally synthesized from compounds found in pit viper venom, they inhibit angiotensin-converting enzyme (ACE), a component of the blood pressure-regulating renin-angiotensin system.

Angiotensin-converting enzyme inhibitors (ACE inhibitors) reduce the activity of the renin-angiotensin-aldosterone system. One mechanism for maintaining the blood pressure is the release of a protein called renin from cells in the kidney (to be specific, the juxtaglomerular apparatus). This produces another protein, angiotensin, which signals the adrenal gland to produce aldosterone. This system is activated in response to a fall in blood pressure (hypotension), as well as markers of problems with the salt-water balance of the body, such as decreased sodium concentration in the distal tubule of the kidney, decreased blood volume and stimulation of the kidney by the sympathetic nervous system. In such situations, the kidneys release renin, which acts as an enzyme and cuts off all but the first 10 amino acid residues of angiotensinogen (a protein made in the liver, and which circulates in the blood). These 10 residues are then known as angiotensin I. Angiotensin I is then converted to angiotensin II by angiotensin converting enzyme (ACE).

Angiotensin converting enzyme inhibitors (ACE inhibitors) block the conversion of angiotensin I to angiotensin II. They, therefore, lower arteriolar resistance and increase venous capacity; increase cardiac output, cardiac index, stroke work, and volume; lower renovascular resistance; and lead to increased natriuresis (excretion of sodium in the urine).

Based on the disease condition and diagnosis, the physicians tend to prescribe a combination of two or more anti-hypertensive drugs to a patient. Such combinations are expected to provide a better control over various cardiovascular diseases. The said combinations can be given as two separate drugs administered separately at same time or at different timings. Several fixed dose combinations of anti-hypertensive drugs are available in the market. Wherever possible, a fixed dose combination is used by physicians to simplify the dosing regimen. Some of the commercially available cardiovascular drug combinations include Lopressor HCT® (Metoprolol and Hydrochlorthiazide); Valturna® (Aliskiren hemifumarate and Valsartan); Exforge HCT® (Amlodipine besylate, Hydrochlorothiazide); Exforge® (Amlodipine besylate and Valsartan); Diovan HCT® (Hydrochlorothiazide and Valsartan); Twynsta® (Amlodipine besylate and Telmisartan); Micardis HCT® (Hydrochlorothiazide and Telmisartan); Hyzaar® (Hydrochlorothiazide and Losartan potassium); Avalide® (Hydrochlorothiazide and Irbesartan); Atacand HCT® (Candesartan cilexetil and Hydrochlorothiazide); Tribenzor® (Amlodipine besylate, Hydrochlorothiazide and Olmesartan medoxomil); Azor® (Amlodipine besylate and olmesartan medoxomil); Benicar HCT® (Hydrochlorothiazide and Olmesartan medoxomil); Vaseretic® (Enalapril maleate and Hydrochlorothiazide); Quinaretic® (Hydrochlorothiazide and Quinapril hydrochloride); Accuretic® (Hydrochlorothiazide and Quinapril hydrochloride); Zestoretic® (Hydrochlorothiazide and Lisinopril); Prinzide® (Hydrochlorothiazide and Lisinopril); Lotrel® (Amlodipine besylate and Benazepril hydrochloride); Lotensin HCT® (Benazepril hydrochloride and Hydrochlorothiazide); Capozide® (Captopril and Hydrochlorothiazide); and Tarka® (Trandolapril and Verapamil hydrochloride). However, these fixed dose combinations does not provide physician an option to modulate the dose of drugs within these fixed dose combinations according to need of a patient.

These cardiovascular combinations are also prescribed along with other drugs such as cardioprotectant, platelet aggregation inhibitors, anticoagulants, antipsychotics, etc. This multiple medication administration, complex drug regimen, and frequent dose administration complicates the patient's compliance. Since cardiovascular disorders are often chronic disorders, complex drug regimen involving several drugs has a negative impact on patient's life leading to non-compliance. Most of the patient's tend to forget dosage regimen quite often. Further, it becomes difficult for the physician to prescribe appropriate doses of different drugs when used in combination. Moreover, because of the complexity of dosage regimen, it becomes difficult for the pharmacist to explain the treatment regimen to the patient being treated. Thus, non-compliance occurs at all three levels i.e. at physician, pharmacist and patient's level. In order to improve compliance there is a need of an appropriate compliance package, which is self explanatory to patient comprising appropriate fixed dose combinations.

U.S. Pat. No. 4,572,909 discloses amlodipine; U.S. Pat. No. 4,446,325 discloses aranidipine; U.S. Pat. No. 4,772,596 discloses azelnidipine; U.S. Pat. No. 4,220,649 discloses barnidipine; U.S. Pat. No. 4,448,964 discloses benidipine; U.S. Pat. No. 5,856,346 discloses clevidipine; U.S. Pat. No. 4,466,972 discloses isradipine; U.S. Pat. No. 4,885,284 discloses efonidipine; and U.S. Pat. No. 4,264,611 discloses felodipine.

U.S. Pat. No. 5,399,578 discloses Valsartan; European Patent No. 0 502 314 discloses Telmisartan; U.S. Pat. No. 5,138,069 discloses Losartan; U.S. Pat. No. 5,270,317 discloses Irbesartan; U.S. Pat. Nos. 5,583,141 and 5,736,555 discloses Azilsartan; U.S. Pat. No. 5,196,444 discloses Candesartan; U.S. Pat. No. 5,616,599 discloses Olmesartan; and U.S. Pat. No. 5,185,351 discloses Eprosartan.

U.S. Pat. No. 4,374,829 discloses enalapril; U.S. Pat. No. 4,587,258 discloses ramipril; U.S. Pat. No. 4,344,949 discloses quinapril; U.S. Pat. No. 4,508,729 discloses perindopril; U.S. Pat. No. 4,374,829 discloses lisinopril; U.S. Pat. No. 4,410,520 discloses benazepril; U.S. Pat. No. 4,508,727 discloses imidapril; U.S. Pat. No. 4,316,906 discloses zofenopril; U.S. Pat. Nos. 4,046,889 and 4,105,776 discloses captopril; and U.S. Pat. No. 4,337,201 discloses fosinopril.

Pharmaceutical compositions comprising beta-adrenergic blockers and/or calcium channel blockers are disclosed in following patent and non-patent literature.

Chinese Patent Application No. 101249083 discloses a twice-a-day sustained-release matrix preparation containing amlodipine and metoprolol, wherein 25 to 45 percent of the drug is released in a first hour, 45 to 75 percent in a fourth hour, and more than 75 percent in an eighth hour.

PCT Patent Application No. 1999018957 discloses a pharmaceutical combination of atenolol with amlodipine besylate.

U.S. Pat. No. 4,942,040 discloses a pharmaceutical preparation giving a controlled and extended release of both a dihydropyridine, e.g. felodipine and a 3-adrenoreceptor antagonist, namely metoprolol.

Kumaravelrajan et al., (Lipids in Health and Disease (2011), 10-51) discloses a controlled porosity osmotic pump tablet (CPOP) system to deliver Nifedipine (NP) and Metoprolol (MP) in a controlled manner up to 12 hours. The developed osmotic system was effective in the multi-drug therapy of hypertension.

Trenkwalder et al., (Journal of human hypertension, (1995), 9 (2), S37-42) discloses an extended-release (ER) formulation, combining felodipine, 5 mg, and metoprolol, 50 mg.

CTRI/2008/091/000190 discloses a randomised, open-label; parallel group, multicentric study comparing the efficacy and safety of fixed-dose-combinations of Metoprolol XL plus Amlodipine with individual components of the combination.

CTRI/2009/091/000269 discloses a single arm trial assessing the efficacy and tolerability of a fixed-dose combination of metoprolol and amlodipine in essential hypertension.

Pharmaceutical compositions comprising beta-adrenergic blockers and/or angiotensin II receptor blockers are disclosed in following patent and non-patent literature.

PCT Patent Application No. 201128016 discloses a formulation comprising an immediate-release compartment including beta-adrenergic blockers nebivolol and an extended-release compartment including angiotensin II receptor blockers losartan.

Indian Patent Application No. 2205/MUM/2007 discloses a pharmaceutical combination comprising $\beta_1$ receptor antagonist nebivolol and angiotensin II receptor blocker telmisartan.

Indian Patent Application No. 1324/MUM/2008 discloses a pharmaceutical composition of angiotensin II receptor blocker such as losartan potassium and a beta-selective adrenoreceptor blocking agent metoprolol succinate in monolithic matrix technology.

CTRI/2010/091/001438 discloses a single arm trial to evaluate the safety and efficacy of fixed dose combination of olmesartan and metoprolol succinate ER in hypertensive patients with cardiovascular disease.

Pharmaceutical compositions comprising beta-adrenergic blockers and/or ACE inhibitors are disclosed in following patent and non-patent literature.

PCT Patent Application No. 2007010501 ('501) discloses a once a day pharmaceutical composition comprising a beta-blocker and ACE inhibitor, wherein the beta blocker is present in an extended release form and the ACE inhibitor is present in an immediate release form. The composition may exhibit release of metoprolol over a period of 12-13 hours.

U.S Patent Application No. 20050032879 ('879) discloses use of a beta-blocker and an ACE-inhibitor in combination for the treatment of hypertension. The release of drugs from the dosage form may be provided over a period of 12-15 hours and therefore the combination may not provide adequate synergistic effects.

Metoprolol has been classified as a class I substance according to the Biopharmaceutics Classification Scheme (BCS), meaning that it is highly soluble and highly permeable. The drug is readily and completely absorbed throughout the whole intestinal tract but is subject to extensive first pass metabolism resulting in incomplete bioavailability (about 50%). Amlodipine besylate, a representative example in class of calcium channel blockers is slightly soluble in water and sparingly soluble in ethanol. Amlodipine also undergoes extensive first pass metabolism. Thus, formulating a once-a-day dosage form of highly water soluble metoprolol in a fixed dose combination comprising an extended release metoprolol and highly water soluble actives belonging to calcium channel blockers, angiotensin II receptor blockers and ACE inhibitors is a challenging task for a pharmacist.

None of the above mentioned prior arts provides a once-a-day fixed dose formulation comprising an extended release metoprolol with a calcium channel blocker, angiotensin II receptor blocker or ACE inhibitor, which is safe and has an enhanced therapeutic effect over the existing individual drug therapy. The prior arts disclosing pharmaceutical composition comprising metoprolol in combination with one or more calcium channel blocker, angiotensin II receptor blocker or ACE inhibitor does not provide a once-a-day dosage form with desired synergistic therapeutic effect. The combination disclosed in the prior arts also does not address the uniform release and bioavailability related aspects of either of metoprolol, calcium channel blocker, calcium channel blocker, angiotensin II receptor blocker or ACE inhibitor when formulated into a once-a-day dosage form. Present inventors developed a matrix dosage form comprising combination of $\beta_1$ blocker drugs in combination with calcium channel blocker, angiotensin II receptor blocker or ACE inhibitor. The release profile obtained from matrix tablets was erratic and varied from batch to batch. It was found that due to highly soluble and highly permeable nature of metoprolol, it is difficult to formulate and achieve an extended release once a day formulation in matrix dosage form. Further, preparing a fixed dose combination comprising an extended release metoprolol was also a major challenge as it was difficult to achieve the desired therapeutic release of the combination when combined into a single unit dosage form. Therefore, there is an ongoing need for the development of new dosage forms comprising an extended release metoprolol with calcium channel blocker, angiotensin II receptor blocker or ACE inhibitor which are safe and effective.

SUMMARY OF THE INVENTION

In one aspect, the present invention provides a pharmaceutical dosage form for treatment of cardiovascular disorders suitable for once daily administration comprising a fixed dose combination of metoprolol in extended release form and one or more calcium channel blockers along with one or more rate controlling excipients.

In another aspect, the present invention provides a pharmaceutical dosage form for treatment of cardiovascular disorders suitable for once daily administration comprising a fixed dose combination of metoprolol in extended release form and one or more one or more angiotensin II receptor blockers along with one or more rate controlling excipients.

In another aspect, the present invention provides a pharmaceutical dosage form for treatment of cardiovascular disorders suitable for once daily administration comprising a fixed dose combination of metoprolol in extended release form and one or more ACE inhibitors along with one or more rate controlling excipients.

In another aspect, the present invention provides a once-a-day pharmaceutical dosage form for treatment of cardiovascular disorders, wherein the dosage form comprises a fixed dose combination of about 25 mg to 200 mg of metoprolol in extended release form and about 2.5 mg to 800 mg of one or more calcium channel blockers.

In another aspect, the present invention provides a once-a-day pharmaceutical dosage form for treatment of cardiovascular disorders, wherein the dosage form comprises a fixed dose combination of about 25 mg to 200 mg of metoprolol in extended release form and about 20 mg to about 800 mg of angiotensin II receptor blocker.

In another aspect, the present invention provides a once-a-day pharmaceutical dosage form for treatment of cardiovascular disorders, wherein the dosage form comprises a fixed dose combination of about 25 mg to 200 mg of metoprolol in extended release form and about 1 mg to about 100 mg of ACE inhibitors.

In another aspect, the once-a-day pharmaceutical dosage form for treatment of cardiovascular disorders exhibits immediate release of calcium channel blocker, angiotensin II receptor blocker and ACE inhibitor.

In another aspect, the extended release metoprolol component of the dosage form comprises a water swellable or water insoluble inert core coated with one or more rate controlling excipient.

In another aspect, the water swellable core comprises microcrystalline cellulose, hydroxypropyl methylcellulose, starch or mixtures thereof.

In another aspect, the water insoluble inert core comprises silicon dioxide, glass particles, plastic resin particles or mixtures thereof.

In another aspect, the rate controlling excipient comprises one or more polymeric rate controlling excipients, non-polymeric rate controlling excipients, or mixtures thereof.

In another aspect, the polymeric rate controlling excipient is selected from the group consisting of one or more of cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof and non-polymeric rate controlling excipient is selected from the group consisting of fat, wax, fatty acid, fatty acid ester, long chain monohydric alcohol or their ester or any combinations thereof.

In another aspect, the present invention provides a once-a-day pharmaceutical dosage form for treatment of cardiovascular disorders, wherein the dosage form comprises a fixed dose combination of metoprolol in extended release form and an agent selected form one or more calcium channel blockers, one or more angiotensin II receptor blockers and one or more ACE inhibitors along with one or more rate controlling excipients; characterized in that said composition exhibits a dissolution profile such that less than 6% of metoprolol or its salt is released within 1 hour and 25%-50% of metoprolol or its salt is released within 6 hours and at least 90% of metoprolol is released after 20 hours when the release rate is measured in USP Type 2 Dissolution Apparatus 2 (paddle, 50 rpm) using 500 ml of pH 6.8 phosphate buffer at 37° C.±0.5° C. as dissolution medium.

In another aspect, the pharmaceutical composition comprises pharmaceutically acceptable excipients selected from one or more diluent, binder, glidant, solubilizer, lubricants, disintegrants, colorants, suspending agent, thickener or taste masking agent.

In another aspect, the pharmaceutical dosage form is in the form of a tablet, a capsule, granules, a tablet in tablet, tablet/s in capsule, granules in capsule, an orally disintegrating tablet, a bilayer tablet, a trilayer tablet, an in-lay tablet, or suspension.

In another aspect, the present invention provides a method of treating one or more disorders selected from hypertension, congestive heart failure, angina, myocardial infarction, arteriosclerosis, diabetic nephropathy, diabetic cardiac myopathy, renal insufficiency, peripheral vascular disease, left ventricular hypertrophy, cognitive dysfunction, and chronic heart failure, wherein the method comprises administering a once-a-day pharmaceutical dosage form comprising a fixed dose combination of an metoprolol in extended release form and an agent selected form one or more calcium channel blockers, one or more angiotensin II receptor blockers and one or more ACE inhibitors along with one or more rate controlling excipients to a patient in need of said treatment.

Embodiments of the pharmaceutical composition may include one or more of the following features. For example, the pharmaceutically acceptable excipients may include diluents, disintegrants, binders, bulking agents, anti-adherents, anti-oxidants, buffering agents, colorants, flavoring agents, coating agents, plasticizers, stabilizers, preservatives, lubricants, glidants, chelating agents, and the like known to the art used either alone or in combination thereof.

DETAILED DESCRIPTION OF THE INVENTION

The present inventors while working on the development of pharmaceutical composition comprising a fixed dose combination of an extended release metoprolol with calcium channel blockers, angiotensin II receptor blockers, or ACE inhibitors, surprisingly found that the pharmaceutical composition of the present invention provides a predictable and uniform dissolution profile resulting in therapeutically effective release of the actives over a period of about 24 hours.

The present invention provides once-a-day fixed dose pharmaceutical composition of an extended release metoprolol and an active agent selected from calcium channel blockers, angiotensin II receptor blockers, and ACE inhibitors. The combinations are not only safe and effective medication for treatment of cardiovascular disease, but are also found to be synergistic with enhanced efficacy. This increased efficacy simplifies the management of cardiovascular diseases.

The present inventors have now developed a safe and effective once-a-day therapeutically synergistic pharmaceutical composition comprising metoprolol in extended release form and an agent selected from one or more calcium channel blockers, one or more angiotensin II receptor blockers, and one or more ACE inhibitors. From the preliminary studies, inventors have surprisingly found that the combination therapy results in at least 10% improvement in individual's response when compared to monotherapy.

The term "metoprolol", as used herein, refers to a metoprolol base, or any pharmaceutically acceptable salt thereof. In an embodiment, the metoprolol salt is succinate salt or tartrate salt.

In an embodiment, the fixed dosage form comprises metoprolol succinate 23.75 mg, 47.5 mg, 95 mg and 190 mg equivalent to 25 mg, 50 mg, 100 mg and 200 mg of metoprolol tartrate or equivalent to 9.75 mg, 19.5 mg, 39 mg and 78 mg of metoprolol base respectively.

The term "calcium channel blocker", as used herein, refers to calcium channel blocker base, or any pharmaceutically acceptable salt or ester thereof.

The term "angiotensin II receptor blocker", as used herein, refers to angiotensin II receptor blocker base, or any pharmaceutically acceptable salt or ester thereof.

The term "angiotensin converting enzyme inhibitor" or "ACE inhibitor", as used herein, refers to angiotensin converting enzyme inhibitor base, or any pharmaceutically acceptable salt or ester thereof.

As used herein, the term "salt" refers to any pharmaceutically acceptable salt (e.g., acid or base) of a compound of the present invention, which upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, digluconate, dodecylsulfate, cyclopentanepropionate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

As used herein, the term "ester" refers to any pharmaceutically acceptable ester of a compound of the present invention, which upon administration to a subject is capable of providing a compound of this invention or an active metabolite or residue thereof. Representative examples of ester include medoxomil, cilexetil, and the like.

For the purpose of present invention, "once-a-day" means that the composition of the present invention is administered only once over a 24 hour period thereby providing therapeutically beneficial blood levels of the active agents.

The term "fixed dose combination", as used herein, refers to a combination of two or more separate active agents, combined in a single unit dosage form, in defined doses.

The term "compliance" describes willingness or degree to which a patient correctly follows the prescribed course of treatment.

The term "therapeutically synergistic", as used herein, refers to a therapeutic effect achieved by a fixed dose combination treatment that exceeds the optimal effect achieved by monotherapy associated with the same drugs used in the combination. For example, X is the therapeutic effect obtained by "A" drug and Y is the therapeutic effect obtained by "B" drug on administration, thus when "A" and "B" drugs are given together, then the expected therapeutic effect would be "X+Y" but when the therapeutic effect achieved by co-administration of both the drugs in a fixed dose combination exceeds "X+Y" i.e. "(X+Y)*Z", wherein Z is more than 1, the combination is said to be therapeutically synergistic.

The phrase "inert core," as used herein, includes core that is water insoluble and non-swellable.

The phrase "insoluble," as used herein, refers to inert core, which does not dissolve in water.

The phrase "non-swellable," as used herein, refers to inert core having 20% or less swelling after 24 hours.

The term 'inlayed tablet' or 'inlay tablet' as used herein refers to a type of a layered tablet in which instead of the core tablet being completely surrounded by a coating, the top surface is completely exposed.

The term 'inlayed in said layer' is used herein to mean that the tablet of metoprolol may be present at any position in said layer.

The term "bioavailable" as used herein, includes, but is not limited to the rate and extent to which the active agent/s become available to the site of action after administration.

The term "Cmax" is the highest plasma concentration of the drug attained within the dosing interval.

The term "Tmax" is the time period, which elapses after administration of the dosage form at which the plasma concentration of the active agent attains the highest plasma concentration within the dosing interval.

The term "$AUC_{0-t}$" as used herein, means area under plasma concentration-time curve from drug administration to last observed concentration at time t.

The term "$AUC_{0-\alpha}$" as used herein, means area under the plasma concentration-time curve extrapolated to infinite time.

The term "mean", when preceding a pharmacokinetic value (e.g. mean Tmax) represents the mean value of the pharmacokinetic value taken from a population of patients or healthy volunteers.

The present invention provides once-a-day therapeutically synergistic pharmaceutical dosage form for treatment of cardiovascular disorders, wherein the dosage form comprises a fixed dose combination of an extended release metoprolol with an agent selected from one or more calcium channel blockers, one or more angiotensin II receptor blockers and one or more angiotensin converting enzyme inhibitors along with one or more rate controlling excipients.

The calcium channel blockers may be selected from, but not limited to one or more of amlodipine, bepridil, clentiazem, diltiazem, fendiline, gallopamil, mibefradil, prenylamine; semotiadil, terodiline, elgodipine, lacidipine, lercanidipine, manidipine, nicardipine, nifedipine, nilvadipine, nimodipine, nisoldipine, nitrendipine, flunarizine, lidoflazine, lomerizine, bencyclane, etafenone, perhexyline, aranidipine, azelnidipine, barnidipine, benidipine, cilnidipine, clevidipine, isradipine, efonidipine, felodipine, pranidipineor, and verapamil.

In an embodiment, the calcium channel blocker is amlodipine or nifedipine or both.

Preferred salt of calcium channel blocker includes amlodipine besylate, bepridil hydrochloride, diltiazem hydrochloride, nicardipine hydrochloride, and verapamil hydrochloride.

The angiotensin II receptor blockers may be selected from, but not limited to one or more of Valsartan, Telmisartan, Losartan, Irbesartan, Azilsartan, Candesartan, Eprosartan, and Olmesartan.

In an embodiment, the angiotensin II receptor blocker is Valsartan or Olmesartan medoxomil or both.

Preferred salt or ester of angiotensin II receptor blocker includes losartan potassium, candesartan cilexetil, olmesartan medoxomil and eprosartan mesylate.

The ACE inhibitors may be selected from, but not limited to one or more of benazepril, captopril, cilazapril, delapril, enalapril, enalaprilat, fosinopril, rentiapril, zabicipril, spirapril, lisinopril, perindopril, ramipril, spiraprilat, trandolapril, zofenopril, and quinapril.

In an embodiment, the ACE inhibitors is Lisinopril or Enalapril, or both.

Preferred salt or ester of ACE inhibitor includes, Benazepril hydrochloride, Enalapril maleate, Fosinopril sodium, Lisinopril dihydrate, Perindopril erbumine, and Quinapril hydrochloride.

In an embodiment, when the once-a-day therapeutically synergistic pharmaceutical dosage form of the present invention comprises metoprolol in extended release form and calcium channel blocker, the amount of metoprolol and calcium channel blocker in the dosage form ranges between about 25 mg to about 200 mg and between about 2.5 mg to about 800 mg respectively.

In a further embodiment, the once-a-day therapeutically synergistic pharmaceutical dosage form comprises an extended release metoprolol and calcium channel blocker in following combinations:

| Metoprolol | Doses of "Calcium Channel Blockers" in combination with Metoprolol | | | | | | |
|---|---|---|---|---|---|---|---|
| Doses | Amlodipine | Bepridil | Diltiazem | Isradipine | Nicardipine | Nifedipine | Verapamil |
| 25 mg | 2.5 mg | 200 mg | 30 mg | 5 mg | 20 mg | 400 mg | 40 mg |
| 50 mg | 5 mg | 300 mg | 60 mg | 10 mg | 30 mg | 600 mg | 80 mg |
| 100 mg | 10 mg | | 90 mg | | | 800 mg | 120 mg |
| 200 mg | | | 120 mg | | | | |

In a still further embodiment, the present invention provides a once-a-day therapeutically synergistic unit dosage form comprising a fixed dose combination of 25 mg of metoprolol in extended release form with 2.5 mg of amlodipine, 25 mg of metoprolol in extended release form with 5 mg of amlodipine, 50 mg of metoprolol in extended release form with 5 mg of amlodipine, 50 mg of metoprolol in extended release form with 10 mg of amlodipine, 100 mg of metoprolol in extended release form with 5 mg of amlodipine and 100 mg of metoprolol in extended release form with 10 mg of amlodipine.

In another embodiment, when the once-a-day therapeutically synergistic pharmaceutical dosage form of the present invention comprises extended release metoprolol and ACE inhibitor, the amount of metoprolol and ACE inhibitor in the dosage form ranges between about 25 mg to about 200 mg and between about 1 mg to about 100 mg respectively.

In a further embodiment, the once-a-day therapeutically synergistic pharmaceutical dosage form comprises an extended release metoprolol and ACE inhibitor in following combinations:

| Metoprolol | Doses of "ACE inhibitors" in combination with Metoprolol | | | | | | | | |
|---|---|---|---|---|---|---|---|---|---|
| doses | Benazepril | Captopril | Enalapril | Fosinopril | Lisinopril | Perindopril | Ramipril | Trandolapril | Quinapril |
| 25 mg | 5 mg | 12.5 mg | 2.5 mg | 10 mg | 2.5 mg | 2 mg | 1.25 mg | 1 mg | 5 mg |
| 50 mg | 10 mg | 25 mg | 5 mg | 20 mg | 5 mg | 4 mg | 2.5 mg | 2 mg | 10 mg |
| 100 mg | 20 mg | 50 mg | 10 mg | 40 mg | 10 mg | 8 mg | 5 mg | 4 mg | 20 mg |
| 200 mg | 40 mg | 100 mg | 20 mg | | 20 mg | | 10 mg | | 40 mg |
| | | | | | 40 mg | | | | |

In another embodiment, when the once-a-day therapeutically synergistic pharmaceutical dosage form of the present invention comprises metoprolol in extended release form and angiotensin II receptor blocker, the amount of metoprolol and angiotensin II receptor blocker in the dosage form ranges between about 25 mg to about 200 mg and between about 4 mg to about 800 mg respectively.

In a further embodiment, the once-a-day therapeutically synergistic pharmaceutical dosage form comprises an extended release metoprolol and angiotensin II receptor blocker in following combinations:

| Metoprolol | Doses of "Angiotensin II Receptor Blockers" in combination with Metoprolol | | | | | | |
|---|---|---|---|---|---|---|---|
| Doses | Losartan | Valsartan | Candesartan | Irbesartan | Olmesartan | Telmisartan | Eprosartan |
| 25 mg | 25 mg | 40 mg | 4 mg | 75 mg | 5 mg | 20 mg | 400 mg |
| 50 mg | 50 mg | 80 mg | 8 mg | 150 mg | 20 mg | 40 mg | 600 mg |
| 100 mg | 100 mg | 160 mg | 16 mg | 300 mg | 40 mg | 80 mg | 800 mg |
| 200 mg | | 320 mg | 32 mg | | | | |

In a still further embodiment, the present invention provides a once-a-day therapeutically synergistic unit dosage form comprising a fixed dose combination of 25 mg of metoprolol in extended release form with 80 mg of valsartan, 25 mg of metoprolol in extended release form with 160 mg of valsartan, 50 mg of metoprolol in extended release form with 160 mg of valsartan, 50 mg of metoprolol in extended release form with 320 mg of valsartan, 100 mg of metoprolol in extended release form with 160 mg of valsartan and 100 mg of metoprolol in extended release form with 320 mg of valsartan.

In a still further embodiment, the present invention provides a once-a-day therapeutically synergistic unit dosage form comprising a fixed dose combination of 25 mg of metoprolol in extended release form with 10 mg of lisinopril, 25 mg of metoprolol in extended release form with 20 mg of lisinopril, 50 mg of metoprolol in extended release form with 20 mg of lisinopril, 50 mg of metoprolol in extended release form with 40 mg of lisinopril, 100 mg of metoprolol in extended release form with 20 mg of lisinopril and 100 mg of metoprolol in extended release form with 40 mg of lisinopril.

In a further embodiment of the present invention, the once-a-day therapeutically synergistic unit dosage form comprises a fixed combination of metoprolol in extended release form and active agent selected from one or more calcium channel blockers, one or more angiotensin II receptor blockers, and one or more ACE inhibitors along with one or more rate controlling excipient, wherein calcium channel blocker, angiotensin II receptor blocker or ACE inhibitor exhibits immediate release from the unit dosage form.

In a further embodiment, the present invention provides a once-a-day therapeutically synergistic pharmaceutical dosage form for treatment of cardiovascular disorders comprising a fixed dose combination of metoprolol in extended release form and an active agent selected from one or more calcium channel blockers, one or more angiotensin II receptor blockers, and one or more ACE inhibitors along with one or more rate controlling excipients. The composition comprises an inert core coated with one or more rate controlling excipients. Such inert core compositions are disclosed in PCT Patent Application No. 2007110753 A, and incorporated hereby for reference.

In a further embodiment, the present invention provides a once-a-day therapeutically synergistic pharmaceutical dosage form for treatment of cardiovascular disorders comprising a fixed dose combination of metoprolol in extended release form and an active agent selected from one or more calcium channel blockers, one or more angiotensin II receptor blockers, and one or more ACE inhibitors along with one or more rate controlling excipients, wherein the composition exhibits a dissolution profile such that less than 6% of metoprolol is released within 1 hour; 25% to 50% of metoprolol is released within 6 hours and at least 90% of metoprolol is released after 20 hours when the release rate is measured in USP Type 2 Dissolution Apparatus (paddle, 50 rpm) using 500 ml of pH 6.8 phosphate buffer at 37° C.±0.5° C. as dissolution medium.

As mentioned in several embodiments of the present invention, the rate controlling excipient is polymeric rate controlling excipient or non-polymeric rate controlling excipient, or combination thereof.

Suitable polymeric rate controlling excipients are selected from, but not limited to, one or more of cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof.

Cellulose derivatives include, but not limited to, ethyl cellulose, methylcellulose, hydroxypropylmethylcellulose (HPMC), hydroxypropyl cellulose (HPC), hydroxyethyl cellulose, hydroxymethyl cellulose, hydroxypropyl ethylcellulose, carboxymethylethyl cellulose, carboxyethylcellulose, carboxymethyl hydroxyethylcellulose, hydroxyethyl methyl carboxymethyl cellulose, hydroxyethyl methyl cellulose, carboxymethyl cellulose (CMC), methyl hydroxyethyl cellulose, methylhydroxypropyl cellulose, carboxymethyl sulfoethyl cellulose, sodium carboxymethyl cellulose, or combinations thereof.

Polyhydric alcohols include, but are not limited to, polyethylene glycol (PEG) or polypropylene glycol; or any combinations thereof.

Saccharides, gums and their derivatives include, but not limited to, dextrin, polydextrin, dextran, pectin and pectin derivatives, alginic acid, sodium alginate, polygalacturonic acid, xylan, arabinoxylan, arabinogalactan, starch, hydroxypropyl starch, amylose and amylopectin, CMC agar; guar gum, locust bean gum, xanthan gum, karaya gum, tragacanth, carrageenan, acacia gum, arabic gum or gellan gum or the like; or any combinations thereof.

Vinyl derivatives, polymers, copolymers or mixtures thereof include, but not limited to, polyvinyl acetate, polyvinyl alcohol, mixture of polyvinyl acetate (8 parts w/w) and polyvinylpyrrolidone (2 parts w/w) (Kollidon SR), copolymers of vinyl pyrrolidone, vinyl acetate copolymers, polyvinylpyrrolidone (PVP); or combinations thereof.

Polyalkylene oxides or copolymers thereof include, but not limited to, polyethylene oxide, polypropylene oxide, poly(oxyethylene)-poly (oxypropylene) block copolymers (poloxamers) or combinations thereof.

Maleic acid copolymers include, but not limited to, vinylacetate-maleic acid anhydride copolymer, styrene-maleic acid anhydride copolymer, styrene-maleic acid monoester copolymer, vinylmethylether-maleic acid anhydride copolymer, ethylene-maleic acid anhydride copolymer, vinylbutylether-maleic acid anhydride copolymer, acrylonitrile-methyl acrylate-maleic acid anhydride copolymer, butyl acrylate-styrene-maleic acid anhydride copolymer or the like or any combinations thereof.

Acrylic acid polymers include any suitable polyacrylic acid polymers or carboxyvinyl polymers such as those available under the brand name carbopol. Pharmaceutically acceptable acrylic polymer may be include one or more, but not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly (methyl methacrylate) copolymer, polyacrylamide, aminoalkyl methacrylate copolymer, poly(methacrylic acid anhydride), and glycidyl methacrylate.

Suitable non-polymeric rate controlling excipient includes, but not limited to fat, wax, fatty acid, fatty acid ester, long chain monohydric alcohol or their ester or any combinations thereof.

Waxes are esters of fatty acids with long chain monohydric alcohols. Natural waxes are often mixtures of such esters, and may also contain hydrocarbons. Waxes employed in the present invention include, but are not limited to, natural waxes, such as animal waxes, vegetable waxes, and petroleum waxes, paraffin waxes, microcrystalline waxes, petrolatum waxes, mineral waxes), and synthetic waxes. Specific examples include, but are not limited to spermaceti wax, carnauba wax, Japan wax, bayberry wax, flax wax, beeswax, yellow wax, Chinese wax, shellac wax, lanolin wax, sugarcane wax, candelilla wax, castor wax paraffin wax, microcrystalline wax, petrolatum wax, carbowax, and the like, or mixtures thereof.

Waxes are also monoglyceryl esters, diglyceryl esters, or glyceryl esters (glycerides) and derivatives and mixtures thereof formed from a fatty acid having from about 10 to about 22 carbon atoms and glycerol, wherein one or more of the hydroxyl groups of glycerol are substituted by a fatty acid. Glycerides employed in the present invention include, but are not limited to, glyceryl monostearate, glyceryl distearate, glyceryl tristearate, glyceryl dipalmitate, glyceryl tripalmitate, glyceryl monopalmitate, glyceryl palmitostearate, glyceryl dilaurate, glyceryl trilaurate, glyceryl monolaurate, glyceryl didocosanoate, glyceryl tridocosanoate, glyceryl monodocosanoate, glyceryl monocaproate, glyceryl dicaproate, glyceryl tricaproate, glyceryl monomyristate, glyceryl dimyristate, glyceryl trimyhstate, glyceryl monodecenoate, glyceryl didecenoate, glyceryl tridecenoate, glyceryl behenate (compritol), polyglyceryl diisostearate, lauroyl macrogolglycerides (Gelucire), oleoyl macrogolglycerides, stearoyl macrogolglycerides, mixtures of monoglycerides and diglycerides of oleic acid (Peceol), or combinations thereof.

Fatty acids include, but not limited to, hydrogenated palm kernel oil, hydrogenated peanut oil, hydrogenated palm oil, hydrogenated rapeseed oil, hydrogenated rice bran oil, hydrogenated soybean oil, hydrogenated sunflower oil, hydrogenated castor oil (Lubritab), hydrogenated cottonseed oil, and mixtures thereof. Other fatty acids include, but are not limited to, decenoic acid, docosanoic acid, stearic acid, palmitic acid, lauric acid, myristic acid, or the like, or mixtures thereof.

Long chain monohydric alcohols include, but not limited to, cetyl alcohol, or stearyl alcohol or mixtures thereof.

The water-swellable inert core can comprise hydroxypropyl methylcellulose, microcrystalline cellulose, starch or mixtures thereof.

The water-insoluble inert core may comprise silicon dioxide, glass particles, plastic resin particles or mixtures thereof.

The pharmaceutical dosage form of the present invention further comprises other pharmaceutically acceptable excipient selected from the group consisting of diluent, binder, glidant, solubilizer, stabilizer, lubricants, disintegrants, cushioning agents, suspending agent, thickening agent, sweetners, flavoring agent, or plasticizer.

Examples of suitable diluents include, but not limited to one or more of lactose, lactose monohydrate, mannitol, sucrose, maltodextrin, dextrin, maltitol, sorbitol, xylitol, powdered cellulose, cellulose gum, microcrystalline cellulose, starch, calcium phosphate, or metal carbonate.

Examples of suitable binders include, but not limited to, starch, gums, pregelatinized starch, polyvinyl prrolidone (PVP), copovidone, cellulose derivatives, such as hydroxypropylmethyl cellulose (HPMC), hydroxypropyl cellulose (HPC) and carboxymethyl cellulose (CMC) and their salts.

Suitable lubricants include, but are not limited to, one or more talc, magnesium stearate, calcium stearate, polyethylene glycol, hydrogenated vegetable oils, stearic acid, sodium stearyl fumarate, talc and sodium benzoate.

Compositions of the present invention may include a glidant such as, but not limited to, colloidal silica, silica gel, precipitated silica, or combinations thereof.

Suitable disintegrant may include, but not limited to, one or more of starch, croscarmellose sodium, crospovidone, and sodium starch glycolate.

The solubilizer may include, but not limited to, one or more surfactant, pH modifier, complexing agent, or hydrotropic agent.

Suitable surfactants are those known to ordinary skilled in the art and may include, but not limited to, one or more of amphoteric, non-ionic, cationic or anionic surfactants. Suitable surfactants comprises one or more of sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, poloxamer, cremophore RH 40 and the like.

Suitable pH modifiers include, but not limited to, buffers, amino acids or amino acid sugars.

The complexing agents include cyclodextrin class of molecules, such as cyclodextrins containing from six to twelve glucose units, especially, alpha-cyclodextrin, beta-cyclodextrin, gamma-cyclodextrin, or their derivatives, such as hydroxypropyl beta cyclodextrins, or mixtures thereof. The complexing agents may also include cyclic amides, hydroxyl benzoic acid derivatives as well as gentistic acid.

Suitable plasticizers include, but not limited to, one or more of diethyl phthalate, triethyl citrate, acetyl tributyl citrate, dibutyl phthalate, triacetin, propylene glycol, and polyethylene glycol.

The solvents comprise one or more of dichloromethane, acetone, ethanol, methanol, isopropyl alcohol, water or mixture thereof.

Suitable cushioning agents include, but are not limited to, one or more of PEG, and colloidal silicon dioxide.

Suitable thickening agents or viscosity modifiers may include, but are not limited to, one or more of methylcellulose, carboxymethylcellulose, microcrystalline cellulose, ethylcellulose, hydroxyethylcellulose, hydroxypropylcellulose, hydroxypropylmethylcellulose, alginate, carageenan, xanthan gum, acacia, tragacanth, locust bean gum, guar gum, carboxypolymethylene, polyvinyl pyrrolidone, polyvinyl alcohol, poloxamer, magnesium aluminum silicate (veegum), bentonite, hectorite, povidone, maltitol, chitosan or combination thereof and the like.

Preservatives may include, but are not limited to, one or more of sodium benzoate, sorbates, such as potassium sorbate, salts of edetate (also known as salts of ethylenediaminetetraacetic acid or EDTA, such as disodium edetate), benzaldionium chloride, parabens and the like.

The formulations of the invention optionally include one or more stabilizing agents to increase the stability and/or compatibility of the suspension when formulated into a dosage form. Suitable stabilizing agents are suspending agents, flocculating agents, thickening agents, gelling agents, buffering agents, antioxidants, preservatives, antimicrobial agents, and mixtures thereof. Ideally, the agent acts to minimize irreversible aggregation of suspended particles, and to maintain proper flow characteristics to ease manufacturing processes, e.g., to ensure that the formulation can be readily pumped and filled into desired container.

Suitable suspending agents may include, but are not limited to, one or more from cellulose derivatives, clays, natural gums, synthetic gums, or other agents known in the art. Specific suspending agents, by way of example, include microcrystalline cellulose, sodium carboxymethylcellulose, powdered cellulose, ethymethylcellulose, hydroyxypropyl methylcellulose, methylcellulose, ethylcellulose, ethylhydroxy ethylcellulose, hydroxypropyl cellulose, attapulgite, bentonite, hectorite, montmorillonite, silica gel, fumed silicon dioxide, colloidal silicon dioxide, acacia, agar, carrageenan, guar gum, locust bean gum, pectin, sodium alginate, propylene glycol alginate, tamarind gum, xanthan gum, carbomer, povidone, sodium starch glycolate, starches, tragacanth, magnesium aluminum silicate, aluminum silicate, magnesium silicate, gelatin, glycyrrhizin and the like. These suspending agents can further impart different flow properties to the suspension. The flow properties of the suspension can be Newtonian, plastic, pseudoplastic, thixotropic or combinations thereof. Mixtures of suspending agents may also be used to optimize flow properties and viscosity.

Suitable buffering agents may include, but are not limited to, one or more of a bicarbonate salt of a Group IA metal, an alkali earth metal buffering agent, amino acids, an acid salt of an amino acid, an alkali salt of an amino acid, and combinations of any of the foregoing.

Moreover, the composition of the invention optionally include usual auxiliaries known in the art such as saliva stimulating agents like citric acid, lactic acid, malic acid, succinic acid, ascorbic acid, adipic acid, fumaric acid, tartaric acids; cooling sensation agents like maltitol, monomenthyl succinate, ultracool; stabilizers like gums, agar; taste masking agents like acrylic polymers, copolymers of acrylates, celluloses, resins; coloring agents like titanium dioxide, natural food colors, dyes suitable for food, drug and cosmetic applications; preservatives like alpha-tocopherol, citric acid, butylated hydroxytoluene, butylated hydroxyanisole, ascorbic acid, fumaric acid, malic acid, sodium ascorbate or ascorbic acid palmitate or effervescing agents like citric acid, tartaric acid, sodium bicarbonate, sodium carbonate and the like.

The dosage form of the present invention may be in form of a tablet, a capsule, granules, a tablet in tablet, an orally disintegrating tablet, pellets, tablet/s in capsule, granules/pellets in capsule, a bilayer tablet, a trilayer tablet, an in-lay tablet or suspension.

The tablet-in-tablet dosage form of the invention may be prepared by compressing metoprolol with one or more rate controlling excipient to form a core tablet; and compressing one or more calcium channel blockers or one or more angiotensin receptor blockers or one or more ACE inhibitors optionally along with one or more pharmaceutically acceptable excipient onto said core tablet to form a compressed outer tablet.

In an embodiment, the tablet-in-tablet dosage form is be prepared by blending metoprolol with rate controlling excipient and other pharmaceutically acceptable excipients. The prepared blend was compressed to form a core tablet. Separately, calcium channel blocker, angiotensin receptor blocker, or ACE inhibitor is blended with one or more pharmaceutically acceptable excipients. Some portion of the above blend is placed in die and the core tablet was placed in center of the blend, the remaining blend is filled in die and compressed such that the metoprolol tablet forms inner tablet and calcium channel blocker, angiotensin receptor blocker or ACE inhibitor forms outer tablet.

The once-a-day dosage form of the invention may also be prepared by compressing metoprolol with one or more rate controlling excipient to form a core and an active agent selected from calcium channel blocker, angiotensin receptor blocker and ACE inhibitor forming outer coating with one or more pharmaceutically acceptable excipients.

In another embodiment, the once-a-day dosage form is prepared by blending metoprolol with rate controlling excipient and one or more other pharmaceutically acceptable excipients. The prepared blend is compressed to form tablets. The formed tablets then coated with dispersion comprising an agent selected from calcium channel blocker, angiotensin receptor blocker and ACE inhibitor, dissolved or dispersed in suitable solvent system along with one or more pharmaceutically acceptable excipient. The outer coating may completely or partially surround the metoprolol tablet.

In another embodiment, the once-a-day dosage form may be prepared by blending two portions with one or more pharmaceutically acceptable excipients followed by compression. First portion may be prepared by coating the inert core with a solution or suspension of metoprolol in a solvent. The metoprolol drug layer is further coated with one or more release-controlling layer(s). Second portion may be prepared by coating one or more calcium channel blocker, angiotensin receptor blocker or ACE inhibitor on an inert core, optionally along with one or more rate controlling layers.

In another embodiment, the once-a-day dosage form may be prepared by blending two portions with one or more pharmaceutically acceptable excipients followed by compression. The first portion was prepared by coating the inert core with a dispersion comprising metoprolol, one or more rate controlling excipients in a solvent. The coated inner core can further be coated with one or more rate controlling layers or seal coat. The second portion was prepared by coating the inert core with a dispersion comprising a calcium channel blocker, an angiotensin receptor blocker or an ACE inhibitor in a solvent.

In an embodiment, the once-a-day dosage form may include a tablet comprising an extended release metoprolol with one or more rate controlling excipient, wherein the tablet is inlayed in another layer comprising a calcium channel blocker, an angiotensin receptor blocker, or an ACE inhibitor and optionally other pharmaceutically acceptable excipients.

In a further embodiment, the inlayed dosage form can be prepared by blending metoprolol with rate controlling excipient and other pharmaceutically acceptable excipients. The prepared blend was compressed to form a core tablet. One or more agent selected from calcium channel blocker, angiotensin receptor blocker and ACE inhibitor are separately blended with one or more pharmaceutically acceptable excipients. Some portion of the above blend was placed in die and the core tablet was placed in a way such that the upper surface of metoprolol tablet is completely exposed after compression.

In a further embodiment, the once-a-day dosage form may be prepared by compressing a first layer comprising an extended release metoprolol along with one or more rate controlling excipients and a second layer comprising one or more calcium channel blocker, angiotensin receptor blocker or ACE inhibitor, one or more pharmaceutically acceptable excipients and, optionally with rate controlling excipient into a bi-layer tablet.

In a further embodiment, the bi-layer dosage form is prepared by blending metoprolol with rate controlling excipient and other pharmaceutically acceptable excipients. The prepared blend was compressed to form a first layer. Onto this first layer a blend comprising calcium channel blocker, angiotensin receptor blocker or ACE inhibitor with one or more pharmaceutically acceptable excipients is compressed to form a bi-layer tablet.

The present invention further provides a method of treating one or more disorders selected form hypertension, congestive heart failure, angina, myocardial infarction, arteriosclerosis, diabetic nephropathy, diabetic cardiac myopathy, renal insufficiency, peripheral vascular disease, left ventricular hypertrophy, cognitive dysfunction, and chronic heart failure, wherein the method comprises administering a pharmaceutical dosage form of the present invention to a patient in need of such treatment.

In another aspect, the present invention provides a method of treating hypertension, wherein the method comprises administering a pharmaceutical dosage form of the present invention to a patient in need of such treatment.

In an embodiment, a method of treating congestive heart failure comprises administering a pharmaceutical dosage form of the present invention to a patient in need of such treatment.

In another embodiment, a method of myocardial infarction comprises administering a pharmaceutical dosage form of the present invention to a patient in need of such treatment.

The examples given below serve to illustrate embodiments of the present invention. However they do not intend to limit the scope of present invention.

EXAMPLE 1

Metoprolol Succinate ER/Amlodipine Besylate Tablet

TABLE 1

Metoprolol Succinate ER/Amlodipine Besylate; Eq 50 mg Tartrate/10 mg

| Stage | Ingredients | % w/w |
|---|---|---|
| Seal coat I | Micro crystalline cellulose spheres | 0.1-20 |
|  | Ethyl cellulose | 0.01-10 |
|  | Triethyl citrate | 0.001-5 |
| Drug Layering (Metoprolol Succinate) | Metoprolol Succinate | 2-70 |
|  | Opadry Clear | 0.1-20 |
| Extended Release coating-I | Ethyl cellulose | 0.1-20 |
|  | Opadry Clear | 0.1-20 |
| Extended Release coating-II | Eudragit L30-D55 | 0.1-20 |
|  | Triethyl citrate | 0.001-5 |
|  | Talc | 0.1-20 |
| Seal coat II | Opadry Clear | 0.1-20 |
| PEG coating | Polyethylene glycol | 0.1-20 |
| Addition of Drug (Amlodipine Besylate) & Tableting | Amlodipine Besylate | 0.1-30 |
|  | Prosolv SMCC 90 | 10-75 |
|  | Sodium starch glycolate | 0.1-20 |
|  | Polyethylene glycol | 0.1-20 |
|  | Sodium Stearyl Fumarate | 0.1-5 |
| Film coating | Opadry white | 0.1-10 |

Procedure:

Microcrystalline cellulose spheres were given seal coat I of ethyl cellulose. These seal coated pellets were subjected to Metoprolol succinate layering with a binder in aqueous solvent system. Drug layered pellets were provided with Extended Release coating-I using Ethyl cellulose and opadry. An extended release coating-II of Eudragit was given using Plasticizer, triethyl citrate & talc. Seal coat-II was given to Extended Release coated pellets followed by PEG coating in suitable solvent system. These PEG coated pellets was blended with the Prosolv, Amlodipine Besylate, Croscarmellose sodium, PEG & Sodium Stearyl Fumarate and compressed into a tablet. An opadry coat was given to core tablets.

Tablets obtained from example 1 were subjected to dissolution studies. The results of dissolution studies performed are provided in Table 2.

TABLE 2

Dissolution profile

| Dissolution of Metoprolol Succinate Method: 500 mL of pH 6.8 phosphate buffer, USP II apparatus at 50 rpm | | Dissolution of Amlodipine Method: 500 mL of pH 0.01N HCl, USP II apparatus at 75 rpm | |
|---|---|---|---|
| Time points (h) | % Drug dissolved | Time points (min) | % Drug dissolved |
| 1 | 6 | 10 | 89 |
| 2 | 10 | 20 | 95 |
| 4 | 24 | 30 | 96 |
| 6 | 40 | 45 | 97 |
| 8 | 53 | 60 | 98 |
| 10 | 66 | — | — |
| 12 | 75 | — | — |
| 16 | 88 | — | — |
| 20 | 95 | — | — |
| 24 | 98 | — | — |

EXAMPLE 2

Metoprolol Succinate ER/Amlodipine Besylate Tablet

TABLE 3

Metoprolol Succinate ER/Amlodipine Besylate; Eq 25 mg Tartrate/2.5 mg

| Stage | Ingredients | % w/w |
|---|---|---|
| Seal coat I | Micro crystalline cellulose spheres | 0.1-20 |
|  | Ethyl cellulose | 0.01-10 |
|  | Triethyl citrate | 0.001-5 |
| Drug Layering (Metoprolol Succinate) | Metoprolol Succinate | 2-70 |
|  | Opadry Clear | 0.1-20 |
| Extended Release coating-I | Ethyl cellulose | 0.1-20 |
|  | Opadry Clear | 0.1-20 |
| Extended Release coating-II | Eudragit L30-D55 | 0.1-20 |
|  | Triethyl citrate | 0.001-5 |
|  | Talc | 0.1-20 |
| Seal coat II | Opadry Clear | 0.1-20 |
| Drug Layering (Amlodipine Besylate) | Amlodipine Besylate | 0.1-25 |
|  | Opadry Clear | 0.1-40 |
| PEG coating | Polyethylene glycol | 0.1-10 |
| Tableting | Prosolv SMCC 90 | 10-60 |
|  | Croscarmellose sodium | 0.5-15 |
|  | Polyethylene glycol | 0.1-10 |
|  | Sodium Stearyl Fumarate | 0.01-5 |
| Film coating | Opadry white | 0.1-10 |

Procedure:

Microcrystalline cellulose spheres was given seal coat I of ethyl cellulose. These seal coated pellets were subjected to Metoprolol succinate layering with a binder in aqueous solvent system. Drug layered pellets were provided with Extended Release coating-I using Ethyl cellulose and opadry. An Extended Release coating-II of Eudragit was given using Plasticizer, triethyl citrate & talc. Seal coat-II was given to Extended Release coated pellets followed by drug layering of Amlodipine Besylate and PEG coating in suitable solvent system. These PEG coated pellets was blended with the Prosolv, Croscarmellose sodium, PEG & Sodium Stearyl Fumarate and compressed into tablet. An opadry coat was given to core tablets.

Tablets obtained from example 2 were subjected to dissolution studies. The results of dissolution studies performed are provided in Table 4.

TABLE 4

Dissolution profile

| Dissolution of Metoprolol Succinate Method: 500 mL of pH 6.8 phosphate buffer, USP II apparatus at 50 rpm | | Dissolution of Amlodipine Method: 500 mL of pH 0.01N HCl, USP II apparatus at 75 rpm | |
|---|---|---|---|
| Time points (h) | % Drug dissolved | Time points (min) | % Drug dissolved |
| 1 | 6 | 10 | 84 |
| 2 | 9 | 20 | 94 |
| 4 | 25 | 30 | 98 |
| 6 | 39 | 45 | 99 |
| 8 | 61 | 60 | 99 |
| 10 | 68 | — | — |
| 12 | 81 | — | — |
| 16 | 92 | — | — |
| 20 | 98 | — | — |
| 24 | 99 | — | — |

EXAMPLE 3

Metoprolol Succinate ER/Amlodipine Besylate Tablet

TABLE 5

Metoprolol Succinate ER/Amlodipine Besylate; Eq 25 mg Tartrate/5 mg

| Stage | Ingredients | % w/w |
|---|---|---|
| Seal coat I | Microcrystallinecellulose spheres | 0.1-20 |
|  | Ethyl cellulose | 0.01-10 |
|  | Triethyl citrate | 0.001-5 |
| Drug Layering (Metoprolol Succinate) | Metoprolol Succinate | 2-70 |
|  | Opadry Clear | 0.1-20 |
| Extended Release coating-I | Ethyl cellulose | 0.1-20 |
|  | Opadry Clear | 0.1-20 |
| Extended Release coating-II | Eudragit L30-D55 | 0.1-20 |
|  | Triethyl citrate | 0.001-5 |
|  | Talc | 0.1-20 |
| Seal coat II | Opadry Clear | 0.1-20 |
| PEG coating | Polyethylene glycol) | 0.1-10 |
| Tableting | Prosolv SMCC 90 | 10-60 |
|  | Croscarmellose sodium | 0.5-15 |
|  | Polyethylene glycol | 0.1-10 |
|  | Sodium Stearyl Fumarate | 0.01-5 |
| Drug Layering (Amlodipine Besylate) | Amlodipine Besylate | 0.1-50 |
|  | Opadry Clear | 0.1-25 |
| Film coating | Opadry white | 0.1-10 |

Procedure:

Microcrystalline cellulose spheres were given seal coat I of ethyl cellulose. These seal coated pellets were subjected to metoprolol succinate layering with a binder in aqueous solvent system. Drug layered pellets were provided with Extended Release coating-I using Ethyl cellulose and opadry. An Extended Release coating-II of Eudragit was given using Plasticizer, triethyl citrate & talc. Seal coat-II was given to Extended Release coated pellets followed by PEG coating in suitable solvent system. These PEG coated pellets was blended with the Prosolv, Croscarmellose sodium, PEG & Sodium Stearyl Fumarate and compressed into tablet. Prepared metoprolol Succinate core tablets were coated with the Amlodipine Besylate using opadry as a binder. An opadry coat was given to prepared coated tablets.

Tablets obtained from example 3 were subjected to dissolution studies. The results of dissolution studies performed are provided in Table 6.

TABLE 6

Dissolution profile

| Dissolution of Metoprolol Succinate Method: 500 mL of pH 6.8 phosphate buffer, USP II apparatus at 50 rpm | | Dissolution of Amlodipine Method: 500 mL of pH 0.01N HCl, USP II apparatus at 75 rpm | |
|---|---|---|---|
| Time points (h) | % Drug dissolved | Time points (min) | % Drug dissolved |
| 1 | 3 | 10 | 91 |
| 2 | 6 | 20 | 98 |
| 4 | 22 | 30 | 100 |
| 6 | 38 | 45 | 100 |
| 8 | 61 | 60 | 101 |
| 10 | 67 | — | — |
| 12 | 77 | — | — |
| 16 | 89 | — | — |
| 20 | 98 | — | — |
| 24 | 100 | — | — |

EXAMPLE 4

Metoprolol Succinate ER/Valsartan Tablet; Eq 25 Mg Tartrate/160 Mg

TABLE 7

Metoprolol succinate ER/Valsartan Tablet Composition

| Component | Stage | Ingredients | % w/w |
|---|---|---|---|
| Tablet I (Inner core) | Seal coat I | Micro crystalline cellulose spheres | 0.1-20 |
|  |  | Ethyl cellulose | 0.01-20 |
|  |  | Triethyl citrate | 0.001-1 |
|  | Drug Layering (Metoprolol succinate) | Metoprolol succinate | 2-70 |
|  |  | Opadry Clear | 0.1-10 |
|  | Extended Release coating-I | Ethyl cellulose | 0.1-30 |
|  |  | Opadry Clear | 0.1-10 |
|  | Extended Release coating-II | Eudragit L30-D55 | 0.1-10 |
|  |  | Triethyl citrate | 0.001-5 |
|  |  | Talc | 0.1-10 |
|  | Seal coat II | Opadry Clear | 0.1-10 |
|  | PEG coating | Polyethylene glycol | 0.1-10 |
|  | Blending | Prosolv SMCC 90 | 10-80 |
|  |  | Croscarmellose sodium | 0.5-15 |
|  |  | Polyethylene glycol | 0.1-10 |
|  |  | Sodium Stearyl fumarate | 0.01-5 |
| Tablet II (Outer fraction) | Granulation | Valsartan | 5-70 |
|  |  | Micro crystalline cellulose | 5-40 |
|  |  | Hypromellose | 0.1-20 |
|  |  | Crospovidone | 0.1-10 |
|  |  | Silicone dioxide | 0.1-10 |
|  |  | Magnesium stearate | 0.1-5 |
| Coating | Film coating | Opadry white | 0.1-10 |

Procedure:

Process involved tab-in-tab technology where core tablet was prepared by using microcrystalline cellulose spheres were given seal coat I of ethyl cellulose. These seal coated pellets were subjected to metoprolol succinate layering with a binder in aqueous solvent system. Drug layered pellets were provided with Extended Release coating-I using Ethyl cellulose and opadry. An Extended Release coating-II of Eudragit was given using Plasticizer, triethyl citrate & talc. Seal coat-II was given to Extended Release coated pellets followed by PEG coating in suitable solvent system. These PEG coated pellets was blended with the Prosolv, Cross carmellose sodium, PEG & Sodium Stearyl fumarate to obtained core tablet. Outer fraction of tab-in-tab was prepared by blending Valsartan with Microcrystalline cellulose, Hypromellose, Crospovidone, Silicone dioxide & lubricant, Magnesium stearate. Both blend were used to prepare tab-in-tab formulation. Prepared metoprolol succinate/valsartan tablets were coated with the opadry.

Tablets obtained from example 4 were subjected to dissolution studies. The results of dissolution studies performed are provided in Table 8.

TABLE 8

Dissolution profile

| Dissolution of Metoprolol succinate Method: 500 mL of pH 6.8 phosphate buffer, USP II apparatus at 50 rpm | | Dissolution of Valsartan Method: 1000 mL of pH 6.8 phosphate buffer, USP II apparatus at 50 rpm | |
|---|---|---|---|
| Time points (h) | % Drug dissolved | Time points (min) | % Drug dissolved |
| 1 | 5 | 10 | 75 |
| 2 | 7 | 20 | 86 |
| 4 | 21 | 30 | 99 |
| 6 | 39 | 45 | 99 |
| 8 | 61 | 60 | 100 |
| 10 | 68 | — | — |
| 12 | 76 | — | — |
| 16 | 90 | — | — |
| 20 | 98 | — | — |
| 24 | 98 | — | — |

EXAMPLE 5

Metoprolol Succinate ER/Valsartan Tablet; Eq 25 Mg Tartrate/80 Mg

TABLE 9

Metoprolol succinate ER/Valsartan Tablet Composition

| Component | Stage | Ingredients | % w/w |
|---|---|---|---|
| Tablet I (Inner core) | Seal coat I | Micro crystalline cellulose spheres | 0.1-20 |
| | | Ethyl cellulose | 0.01-20 |
| | | Triethyl citrate | 0.001-1 |
| | Drug Layering (Metoprolol succinate) | Metoprolol succinate | 2-70 |
| | | Opadry Clear | 0.1-10 |
| | Extended Release coating-I | Ethyl cellulose | 0.1-30 |
| | | Opadry Clear | 0.1-10 |
| | Extended Release coating-II | Eudragit L30-D55 | 0.1-10 |
| | | Triethyl citrate | 0.001-5 |
| | | Talc | 0.1-10 |
| | Seal coat II | Opadry Clear | 0.1-10 |
| | PEG coating | Polyethylene glycol | 0.1-10 |
| | Blending | Prosolv SMCC 90 | 10-80 |
| | | Croscarmellose sodium | 0.5-15 |
| | | Polyethylene glycol | 0.1-10 |
| | | Sodium Stearyl fumarate | 0.01-5 |
| Tablet II (Outer fraction) | Granulation | Valsartan | 5-70 |
| | | Micro crystalline cellulose | 5-40 |
| | | Hypromellose | 0.1-20 |
| | | Crospovidone | 0.1-10 |
| | | Silicone dioxide | 0.1-10 |
| | | Magnesium stearate | 0.1-5 |

Procedure:

Process involved inlay tablet where core tablet was prepared by using microcrystalline cellulose as core which was given seal coat I using suitable solvent system. These seal coated pellets were subjected to metoprolol succinate layering with a binder in aqueous solvent system. Drug layered pellets were provided with Extended Release coating-I using Ethyl cellulose and opadry in suitable solvent system. An extended release coating-II of Eudragit was given using Plasticizer, triethyl citrate & talc. Seal coat-II was given to Extended Release coating pellets followed by PEG coating in suitable solvent system. These PEG coated pellets was blended with the Prosolv, Cross carmellose sodium, PEG & Sodium Stearyl fumarate to obtained core tablet. Outer fraction of inlay tablet was prepared by granulation of Valsartan with Microcrystalline cellulose, Hypromellose, Crospovidone, Silicone dioxide followed by addition of lubricant, Magnesium stearate. Both blends were used to prepare inlay tablets.

Tablets obtained from example 5 were subjected to dissolution studies. The results of dissolution studies performed are provided in Table 10.

TABLE 10

Dissolution profile

| Dissolution of Metoprolol succinate Method: 500 mL of pH 6.8 phosphate buffer, USP II apparatus at 50 rpm | | Dissolution of Valsartan Method: 1000 mL of pH 6.8 phosphate buffer, USP II apparatus at 50 rpm | |
|---|---|---|---|
| Time points (h) | % Drug dissolved | Time points (min) | % Drug dissolved |
| 1 | 4 | 10 | 76 |
| 2 | 7 | 20 | 84 |
| 4 | 22 | 30 | 96 |
| 6 | 44 | 45 | 98 |
| 8 | 61 | 60 | 98 |
| 10 | 71 | — | — |
| 12 | 80 | — | — |
| 16 | 94 | — | — |
| 20 | 99 | — | — |
| 24 | 100 | — | — |

EXAMPLE 6

Metoprolol Succinate ER/Valsartan Capsule; Eq 50 Mg Tartrate/80 Mg

TABLE 11

Metoprolol succinate ER/Valsartan Tablet Composition

| Component | Stage | Ingredients | % w/w |
|---|---|---|---|
| Metoprolol succinate ER pellets | Seal coat I | Micro crystalline cellulose spheres | 0.1-20 |
| | | Ethyl cellulose | 0.01-20 |
| | | Triethyl citrate | 0.001-1 |
| | Drug Layering (Metoprolol succinate) | Metoprolol succinate | 2-70 |
| | | Opadry Clear | 0.1-10 |
| | Extended Release coating-I | Ethyl cellulose | 0.1-30 |
| | | Opadry Clear | 0.1-10 |
| | Extended Release coating-II | Eudragit L30-D55 | 0.1-10 |
| | | Triethyl citrate | 0.001-5 |
| | | Talc | 0.1-10 |
| | Seal coat II | Opadry Clear | 0.1-10 |
| | Lubrication | Talc | 0.05-5 |
| Valsartan Granules | Granulation | Valsartan | 5-50 |
| | | Micro crystalline cellulose | 1-40 |
| | | Povidone | 0.1-10 |
| | | Crospovidone | 10-50 |
| | | Magnesium stearate | 1-5 |

Procedure:

Microcrystalline cellulose spheres was given seal coat I of ethyl cellulose. These seal coated pellets were subjected to metoprolol succinate layering with a binder in aqueous solvent system. Drug layered pellets were provided with Extended Release coating-I using Ethyl cellulose and opadry. An extended release coating-II of Eudragit was given using Plasticizer, triethyl citrate & talc. Seal coat-II was given to Extended Release coated pellets followed by Seal coating II to obtained metoprolol succinate ER pellets. Valsartan granules were prepared by Wet granulation of Valsartan, microcrystalline cellulose & Crospovidone using povidone as binder followed by drying & lubrication with magnesium stearate.

Tablets obtained from example 6 were subjected to dissolution studies. The results of dissolution studies performed are provided in Table 12.

TABLE 12

Dissolution profile

| Dissolution of Metoprolol succinate Method: 500 mL of pH 6.8 phosphate buffer, USP II apparatus at 50 rpm | | Dissolution of Valsartan Method: 1000 mL of pH 6.8 phosphate buffer, USP II apparatus at 50 rpm | |
|---|---|---|---|
| Time points (h) | % Drug dissolved | Time points (min) | % Drug dissolved |
| 1 | 3 | 10 | 74 |
| 2 | 7 | 20 | 85 |
| 4 | 24 | 30 | 94 |
| 6 | 38 | 45 | 97 |
| 8 | 60 | 60 | 98 |
| 10 | 66 | — | — |
| 12 | 77 | — | — |
| 16 | 89 | — | — |
| 20 | 97 | — | — |
| 24 | 99 | — | — |

EXAMPLE 7

Metoprolol Succinate ER/Lisinopril ER Capsules

TABLE 13

Metoprolol succinate ER/Lisinopril ER Capsules; Eq 50 mg Tartrate/5 mg

| Component | Stage | Ingredients | % w/w |
|---|---|---|---|
| Metoprolol succinate ER pellets | Seal coat I | Micro crystalline cellulose spheres | 0.1-20 |
| | | Ethyl cellulose | 0.01-20 |
| | | Triethyl citrate | 0.001-1 |
| | Drug Layering (Metoprolol succinate) | Metoprolol succinate | 2-40 |
| | | Opadry Clear | 0.1-10 |
| | Extended Release coating-I | Ethyl cellulose | 0.1-30 |
| | | Opadry Clear | 0.1-10 |
| | Extended Release coating-II | Eudragit L30-D55 | 0.1-10 |
| | | Triethyl citrate | 0.001-5 |
| | | Talc | 0.1-10 |
| | Seal coat II | Opadry Clear | 0.1-10 |
| | Lubrication | Talc | 0.1-10 |
| Lisinopril pellets | Drug Layering (Lisinopril) | Micro crystalline cellulose spheres | 0.1-10 |
| | | Lisinopril | 0.1-25 |
| | | Opadry Clear | 0.1-10 |
| | | Talc | 0.1-10 |
| | Lubrication | Talc | 0.01-5 |

Procedure:

Microcrystalline cellulose spheres were given seal coat I of ethyl cellulose. These seal coated pellets were subjected to Metoprolol succinate layering with a binder in aqueous solvent system. Drug layered pellets were provided with Extended Release coating-I using Ethyl cellulose and opadry. An extended release coating of Eudragit was given using Plasticizer, triethyl citrate & talc. Seal coat-II was given to Extended Release coated-II pellets followed by seal coat II & lubrication with talc to obtained metoprolol succinate ER pellets.

To the obtained Lisinopril pellets, microcrystalline cellulose spheres were directly coated with Lisinopril along with opadry as binder. These drug layered pellets were lubricated with talc and filled with metoprolol succinate ER pellets in empty hard gelatin capsule.

Capsules obtained from example 7 were subjected to dissolution studies. The results of dissolution studies performed are provided in Table 14.

TABLE 14

Dissolution study

| Dissolution of Metoprolol succinate Method: 500 mL of pH 6.8 phosphate buffer, USP II apparatus at 50 rpm | | Dissolution of Lisinopril Method: 900 mL of 0.1N HCl, USP II apparatus at 50 rpm | |
|---|---|---|---|
| Time points (h) | % Drug dissolved | Time points (min) | % Drug dissolved |
| 1 | 4 | 10 | 86 |
| 2 | 6 | 20 | 98 |
| 4 | 20 | 30 | 98 |
| 6 | 34 | 45 | 99 |
| 8 | 60 | 60 | 99 |
| 10 | 66 | — | — |
| 12 | 76 | — | — |
| 16 | 89 | — | — |
| 20 | 97 | — | — |
| 24 | 100 | — | — |

EXAMPLE 8

Metoprolol Succinate ER/Enalapril Maleate Tablet

TABLE 15

Metoprolol succinate ER/Enalapril maleate Tablet; Eq 50 mg Tartrate/10 mg

| Stage | Ingredients | % w/w |
|---|---|---|
| Seal coat I | Microcrystallinecellulose spheres | 0.1-20 |
| | Ethyl cellulose | 0.01-20 |
| | Triethyl citrate | 0.001-5 |
| Drug Layering (Metoprolol Succinate) | Metoprolol succinate | 2-70 |
| | Opadry Clear | 0.1-20 |
| Extended Release coating-I | Ethyl cellulose | 0.1-30 |
| | Opadry Clear | 0.1-20 |
| Extended Release coating-II | Eudragit L30-D55 | 0.1-20 |
| | Triethyl citrate | 0.001-5 |
| | Talc | 0.1-20 |
| Seal coat II | Opadry Clear | 0.1-20 |
| PEG coating | Polyethylene glycol | 0.1-20 |
| Granulation | Enalapril maleate | 0.1-30 |
| | Lactose | 1-40 |
| | Sodium bicarbonate | 0.1-30 |
| | Corn starch | 0.1-10 |
| Blending & Tableting | Prosolv SMCC 90 | 10-80 |
| | Pregelatinized starch | 0.1-20 |
| | Polyethylene glycol | 0.1-20 |
| | Sodium Stearyl Fumarate | 0.01-10 |
| Film coating | Opadry white | 0.1-10 |

Procedure:

Microcrystalline cellulose spheres were given seal coat I of ethyl cellulose. These seal coated pellets were subjected to Metoprolol succinate layering with a binder in aqueous solvent system. Drug layered pellets were provided with Extended Release coating-I using Ethyl cellulose and opadry. An Extended Release coating-II of Eudragit was given using plasticizer, triethyl citrate & talc. Seal coat-II was given to Extended Release coated pellets followed by PEG coating in suitable solvent system. Separately, Enalapril Maleate was mixed with lactose and treated with sodium bicarbonate. The sodium bicarbonate treated blend was then granulated using starch paste. Metoprolol succinate PEG coated pellets were blended with the Enalapril maleate granules, Prosolv, Pregelatinized starch, PEG & Sodium Stearyl Fumarate and compressed into a tablet. An opadry coat was given to the core tablets.

Tablets obtained from example 8 were subjected to dissolution studies. The results of dissolution studies performed are provided in Table 16.

TABLE 16

Dissolution study

| Dissolution of Metoprolol succinate Method: 500 mL of pH 6.8 phosphate buffer, USP II apparatus at 50 rpm | | Dissolution of Enalapril maleate Method: 900 mL of pH 6.8 phosphate buffer, USP II apparatus at 50 rpm. | |
|---|---|---|---|
| Time points (h) | % Drug dissolved | Time points (min) | % Drug dissolved |
| 1 | 6 | 10 | 89 |
| 2 | 10 | 20 | 95 |
| 4 | 24 | 30 | 96 |
| 6 | 40 | 45 | 97 |
| 8 | 53 | 60 | 98 |
| 10 | 66 | — | — |
| 12 | 75 | — | — |
| 16 | 88 | — | — |
| 20 | 95 | — | — |
| 24 | 98 | — | — |

EXAMPLE 9

Metoprolol Succinate ER/Enalapril Maleate Tablet

TABLE 17

Metoprolol succinate ER/Enalapril maleate Bilayer Tablet; Eq 100 mg Tartrate/10 mg

| Component | Stage | Ingredients | % w/w |
|---|---|---|---|
| Layer I (Metoprolol succinate) | Seal coat I | Microcrystallinecellulose spheres | 0.1-20 |
| | | Ethyl cellulose | 0.01-20 |
| | | Triethyl citrate | 0.001-5 |
| | Drug Layering (Metoprolol succinate) | Metoprolol succinate | 2-70 |
| | | Opadry Clear | 0.1-20 |
| | Extended Release coating-I | Ethyl cellulose | 0.1-30 |
| | | Opadry Clear | 0.1-20 |
| | Extended Release coating-II | Eudragit L30-D55 | 0.1-20 |
| | | Triethyl citrate | 0.001-5 |
| | | Talc | 0.1-20 |
| | Seal coat II | Opadry Clear | 0.1-20 |
| | PEG coating | Polyethylene glycol | 0.1-10 |
| | Blending | Prosolv SMCC 90 | 10-80 |
| | | Croscarmellose sodium | 0.5-15 |
| | | Polyethylene glycol | 0.1-10 |
| | | Sodium Stearyl Fumarate | 0.01-5 |
| Layer II (Enalapril Maleate) | Granulation | Enalapril maleate | 0.1-25 |
| | | Lactose | 0.1-25 |
| | | Sodium bicarbonate | 0.1-25 |
| | | Starch | 0.1-20 |
| | | Magnesium stearate | 0.1-10 |
| Coating | Film coating | Opadry white | 0.1-10 |

Procedure:

Microcrystalline cellulose spheres were given seal coat I of ethyl cellulose. These seal coated pellets were subjected to metoprolol succinate layering with a binder in aqueous solvent system. Drug layered pellets were provided with Extended Release coating-I using Ethyl cellulose and opadry. An Extended Release coating-II of Eudragit was given using plasticizer, triethyl citrate & talc. Seal coat-II was given to Extended Release coated pellets followed by PEG coating in suitable solvent system. These PEG coated pellets were blended with the Prosolv, Croscarmellose sodium, PEG & Sodium Stearyl Fumarate to obtained layer I blend. Layer II granules were prepared by treated Enalapril Maleate and lactose with sodium bicarbonate. These treated granules were granulated with starch, dried & lubricated with magnesium stearate. Both blend were used to prepare two layers of bilayer tablet. Prepared metoprolol Succinate/Enalapril Maleate bilayer tablets were coated with the opadry.

Tablets obtained from example 9 were subjected to dissolution studies. The results of dissolution studies performed are provided in Table 18.

TABLE 18

Dissolution study

| Dissolution of Metoprolol succinate Method: 500 mL of pH 6.8 phosphate buffer, USP II apparatus at 50 rpm | | Dissolution of Enalapril maleate Method: 900 mL of pH 6.8 phosphate buffer, USP II apparatus at 50 rpm. | |
|---|---|---|---|
| Time points (h) | % Drug dissolved | Time points (min) | % Drug dissolved |
| 1 | 3 | 10 | 65 |
| 2 | 6 | 20 | 85 |
| 4 | 20 | 30 | 96 |
| 6 | 25 | 45 | 98 |
| 8 | 56 | 60 | 98 |
| 10 | 63 | — | — |
| 12 | 73 | — | — |
| 16 | 88 | — | — |
| 20 | 98 | — | — |
| 24 | 99 | — | — |

EXAMPLE 10

Clinical Study

The study methods involved a multicenter, randomized, placebo-controlled, unbalanced factorial study for lowering the blood pressure. Patients, with confirmed diagnosis of stage II hypertension were eligible to participate in the studies. Patients were randomized to one of many treatment groups:

Study 1: Group I were administered extended-release (ER) metoprolol succinate (Eq 25 mg Tartrate, Eq 50 mg Tartrate, Eq 100 mg Tartrate), Group II were administered amlodipine besylate (2.5 mg, 5 mg, 10 mg), Group III were administered metoprolol succinate ER/amlodipine besylate IR (dosages of present invention).

Study 2: Group I were administered extended-release metoprolol succinate (Eq 25 mg tartrate, Eq 50 mg tartrate, Eq100 mg tartrate), Group II were administered valsartan (40 mg, 80 mg, 160 mg, 320 mg), Group III were administered metoprolol succinate ER/Valsartan IR (dosages of present invention).

Study 3: Group I were administered extended-release metoprolol succinate (Eq 25 mg Tartrate, Eq 50 mg Tartrate, Eq 100 mg Tartrate), Group II were administered lisinopril (10 mg, 20 mg, 40 mg), Group III were administered extended release of metoprolol succinate/immediate release lisinopril (dosages of present invention).

After one month of therapy non-responder patients were managed with dose-titration or rescue medication.

Treatment groups in all three studies were well balanced at base line and achieved absolute change at one week from the baseline in blood pressure. It was found that at least 10% improvement in blood pressure (systolic blood pressure and diastolic blood pressure) was attained after 3 months treatment using pharmaceutical dosage form of the present invention.

We claim:

1. A pharmaceutical dosage form for treatment of cardiovascular disorders and suitable for once daily administration; wherein said dosage form comprising a fixed dose combination of: a) metoprolol or a pharmaceutically acceptable salt thereof in extended release form; b) amlodipine or a pharmaceutically acceptable salt thereof in immediate release form and, c) one or more rate controlling polymeric or non-polymeric excipients comprising a cellulosic polymers or derivatives thereof and an acrylic acid polymers or derivatives thereof which form a first and a second layers on metoprolol or a pharmaceutically acceptable salt thereof; said dosage form exhibiting a dissolution profile such that less than 6% of metoprolol or a pharmaceutically acceptable salt thereof is released within 1 hour, between about 25% to about 50% of metoprolol is released within 6 hours and at least 90% of metoprolol is released within 20 hours when the release rate is measured in USP Type 2 Dissolution apparatus in paddle type at 50 rpm using 500 ml of pH 6.8 phosphate buffer at 37° C. ±0.5° C. as dissolution medium.

2. The pharmaceutical dosage form of claim 1, wherein the dosage form comprises about 25 mg to about 200 mg of metoprolol and about 2.5 mg to about 800 mg of amlodipine or a pharmaceutically acceptable salt thereof.

3. A pharmaceutical dosage form for treatment of cardiovascular disorders and suitable for once daily administration; wherein said dosage form comprising a fixed dose combination of: a) metoprolol or a pharmaceutically acceptable salt thereof in extended release form; b) valsartan or olmesartan or a pharmaceutically acceptable salt thereof in immediate release form and, c) one or more rate controlling polymeric or non-polymeric excipients, comprising a cellulosic polymers or derivatives thereof and an acrylic acid polymers or derivatives thereof which form a first and a second layers on metoprolol or a pharmaceutically acceptable salt thereof, said dosage form exhibiting a dissolution profile such that less than 6% of metoprolol or a pharmaceutically acceptable salt thereof is released within 1 hour, between about 25% to about 50% of metoprolol is released within 6 hours and at least 90% of metoprolol is released within 20 hours when the release rate is measured in USP Type 2 Dissolution apparatus in paddle type at 50 rpm using 500 ml of pH 6.8 phosphate buffer at 37° C. ±0.5° C. as dissolution medium.

4. The pharmaceutical dosage form of claim 3, wherein the dosage form comprises about 25 mg to about 200 mg of metoprolol and about 20 mg to about 800 mg of valsartan or olmesartan or a pharmaceutically acceptable salt thereof.

5. A pharmaceutical dosage form for treatment of cardiovascular disorders and suitable for once daily administration, wherein said dosage form comprising a fixed dose combination of: a) metoprolol or a pharmaceutically acceptable salt thereof in extended release form; b) enalapril or a pharmaceutically acceptable salt thereof in immediate release form and, c) one or more rate controlling polymeric or non-polymeric excipients, comprising a cellulosic polymers or derivatives thereof and an acrylic acid polymers or derivatives thereof which form a first and a second layers on metoprolol or a pharmaceutically acceptable salt thereof, said dosage form exhibiting a dissolution profile such that less than 6% of metoprolol or a pharmaceutically acceptable salt thereof is released within 1 hour, between about 25% to about 50% of metoprolol is released within 6 hours and at least 90% of metoprolol is released within 20 hours when the release rate is measured in USP Type 2 Dissolution apparatus in paddle type at 50 rpm using 500 ml of pH 6.8 phosphate buffer at 37° C. ±0.5° C. as dissolution medium.

6. The pharmaceutical dosage form of claim 5, wherein the dosage form comprises about 25 mg to about 200 mg of metoprolol and about 1 mg to about 100 mg of enalapril or a pharmaceutically acceptable salt thereof.

7. A method of treating a disorder selected from one or more of hypertension, congestive heart failure, angina, myocardial infarction, arteriosclerosis, diabetic nephropathy, diabetic cardiac myopathy, renal insufficiency, peripheral vascular disease, left ventricular hypertrophy, cognitive dysfunction, chronic heart failure, wherein the method comprises administering a pharmaceutical dosage form of claim 1, 3 or 5 to a patient in need of such treatment.

* * * * *